(12) United States Patent
Trexler et al.

(10) Patent No.: US 12,702,757 B2
(45) Date of Patent: Aug. 11, 2026

(54) MULTI-CHAMBER SYRINGE

(71) Applicant: Davol Inc., Warwick, RI (US)

(72) Inventors: Jonathan Bruce Trexler, Rehoboth, MA (US); Keith A. Grider, Chicago, IL (US); Antonio Belton, Richton Park, IL (US)

(73) Assignee: Davol Inc., Warwick, RI (US)

( * ) Notice: Subject to any disclaimer, the term of this patent is extended or adjusted under 35 U.S.C. 154(b) by 752 days.

(21) Appl. No.: 18/012,279

(22) PCT Filed: Jun. 22, 2021

(86) PCT No.: PCT/US2021/038398
§ 371 (c)(1),
(2) Date: Dec. 22, 2022

(87) PCT Pub. No.: WO2022/005806
PCT Pub. Date: Jan. 6, 2022

(65) Prior Publication Data

US 2023/0233766 A1 Jul. 27, 2023

Related U.S. Application Data

(60) Provisional application No. 63/046,200, filed on Jun. 30, 2020.

(51) Int. Cl.
*A61M 5/19* (2006.01)
*A61M 5/315* (2006.01)

(52) U.S. Cl.
CPC .......... *A61M 5/19* (2013.01); *A61M 5/31513* (2013.01); *A61M 5/31596* (2013.01)

(58) Field of Classification Search
CPC ................ A61M 5/19; A61M 5/31513; A61M 5/31596; A61M 5/178; A61M 5/31511;
(Continued)

(56) References Cited

U.S. PATENT DOCUMENTS 3,016,896 A * 1/1962 Van Sickle ........... A61M 5/284
604/125
3,749,084 A 7/1973 Cucchiara
(Continued)

FOREIGN PATENT DOCUMENTS

CN 101068585 A 11/2007
DE 10-2020-07011951 U1 12/2007
(Continued)

OTHER PUBLICATIONS

International Search Report and Written Opinion, mailed Sep. 29, 2021 for International Application No. PCT/US2021/038398.
(Continued)

*Primary Examiner* — James D Ponton
*Assistant Examiner* — John A Doubrava
(74) *Attorney, Agent, or Firm* — Wolf, Greenfield & Sacks, P.C.

(57) ABSTRACT

Systems and methods for multi-chambered syringes are described. In some embodiments, a multi-chamber syringe includes a housing with an internal cavity and first and second plungers disposed at least partially within the internal cavity. The first and second plungers are slidably displaceable relative to the housing, and are associated with first and second chambers respectively. A barrier is disposed at least partially between the first and second plungers to form the first and second chambers. The barrier is slidably displaceable relative to the plungers and barrel to selectively place the first and second chambers including first and second materials respectively in fluid communication. When the barrier is displaced, the first and second materials mix in a combined volume of the first and second chambers. Displacing the first plunger, the second plunger, and the barrier may dispense the mixed materials from the combined volume.

24 Claims, 10 Drawing Sheets

(58) Field of Classification Search
CPC ........... A61M 2005/3128; A61M 2005/31598; A61M 2205/0238; A61M 3/005; A61C 5/614; B01F 33/50112; B01F 35/7162; B01F 35/7174; B01F 35/754251
See application file for complete search history.

(56) References Cited

U.S. PATENT DOCUMENTS

| | | | | |
|---|---|---|---|---|
| 4,483,439 | A | 11/1984 | Steigerwald et al. | |
| 4,676,406 | A | 6/1987 | Frischmann et al. | |
| 6,692,468 | B1 | 2/2004 | Waldenburg | |
| 7,216,761 | B2 | 5/2007 | De Vries | |
| 10,279,121 | B2 | 5/2019 | Mojdehbakhsh et al. | |
| 2006/0100587 | A1 | 5/2006 | Bertron et al. | |
| 2008/0234632 | A1 | 9/2008 | Hasegawa | |
| 2010/0121310 | A1 | 5/2010 | Simonton et al. | |
| 2012/0330280 | A1 | 12/2012 | Reynolds et al. | |
| 2015/0025454 | A1 | 1/2015 | Wetzel et al. | |
| 2015/0320935 | A1 | 11/2015 | Dungar et al. | |
| 2016/0106584 | A1* | 4/2016 | Andino .................. | A61M 5/19 604/87 |

FOREIGN PATENT DOCUMENTS

| | | | |
|---|---|---|---|
| EP | 1 093 826 | B1 | 12/2004 |
| JP | 2001-112867 | A | 4/2001 |
| JP | 2004-129695 | A | 4/2004 |
| JP | 2007-506479 | A | 3/2007 |
| JP | 2008-167844 | A | 7/2008 |
| JP | 2008-544821 | A | 12/2008 |

OTHER PUBLICATIONS

International Preliminary Report on Patentability, mailed Jan. 12, 2023 for International Application No. PCT/US2021/038398.
PCT/US2021/038398, Sep. 29, 2021, International Search Report and Written Opinion.
PCT/US2021/038398, Jan. 12, 2023, International Preliminary Report on Patentability.

* cited by examiner

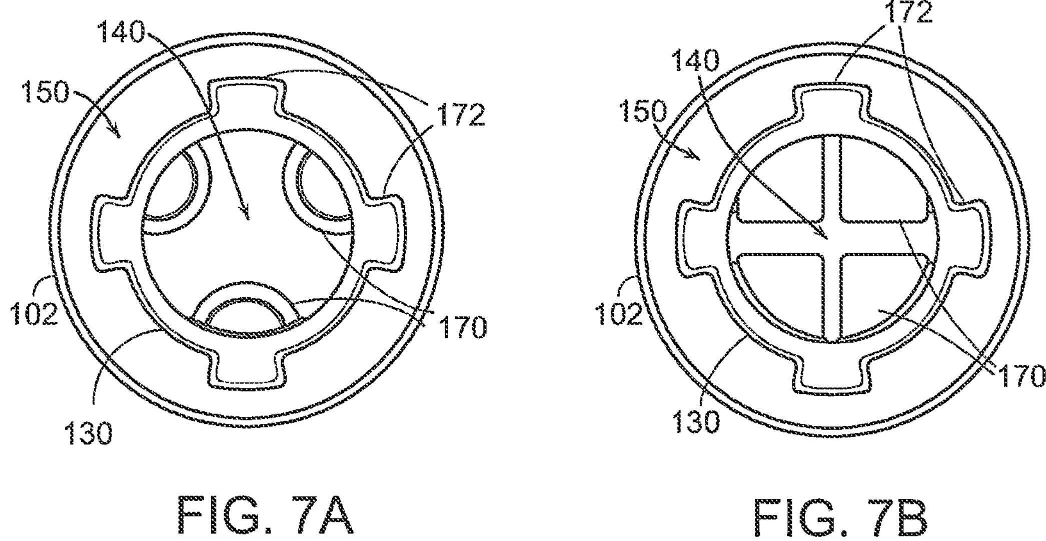
FIG. 7A
FIG. 7B
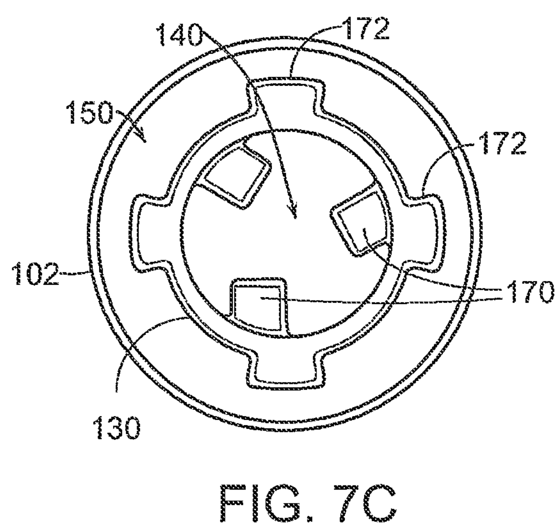
FIG. 7C

MULTI-CHAMBER SYRINGE

CROSS-REFERENCE TO RELATED APPLICATIONS

This application is a national stage filing under 35 U.S.C. § 371 of International Patent Application Serial No. PCT/US2021/038398, filed Jun. 22, 2021, which claims the benefit of priority under 35 U.S.C. § 119(e) of U.S. Provisional Application Ser. No. 63/046,200, filed Jun. 30, 2020. The entire contents of these applications are incorporated herein by reference in their entirety.

FIELD

Disclosed embodiments are related to multi-chambered syringes.

BACKGROUND

A conventional syringe may include a hollow plastic barrel and a plunger. Depressing the plunger may cause a material disposed within an internal cavity of the barrel to be dispensed from the syringe. Retracting the plunger may cause a material to be drawn into the barrel. Syringes are often used within the medical community to dispense a known amount of material at a targeted site. For example, a syringe may be used to inject a precise volume of a therapeutic agent into a patient, or a syringe may be used to deliver a hemostatic matrix to a bleed site.

SUMMARY

In some embodiments, a multi-chamber syringe includes a housing with an internal cavity, first and second plungers, and a barrier. The first plunger and second plungers are disposed at least partially within the internal cavity of the housing, and are slidably displaceable relative to the housing. The barrier is disposed at least partially between the first plunger and the second plunger within the internal cavity of the housing, and the barrier is slidably displaceable relative to the first plunger and the second plunger.

In some embodiments, a method includes displacing a barrier to place a first chamber including a first material in fluid communication with a second chamber including a second material, mixing the first material and the second material in a combined volume of the first chamber and the second chamber, and displacing a first plunger associated with the first chamber, a second plunger associated with the second chamber, and the barrier to dispense the mixed first and second materials from the combined volume.

In some embodiments, a multi-chamber syringe include a housing with an internal cavity, a barrier, and first and second plungers. The barrier is disposed at least partially within the internal cavity of the housing, and is configured to selectively separate a first chamber of the internal cavity from a second chamber of the internal cavity. The first plunger is disposed at least partially within the first chamber, and is slidably displaceable relative to the housing. The second plunger is disposed at least partially within the second chamber, and is slidably displaceable relative to the housing. The first plunger, barrier, and second plunger are configured to form a combined plunger to displace material in a combined volume of the first and second chambers.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIGS. 7A-7C are top cross-sectional views of different embodiments of protrusions configured to promote mixing within a multi-chamber syringe.

DETAILED DESCRIPTION

Figure 1A:
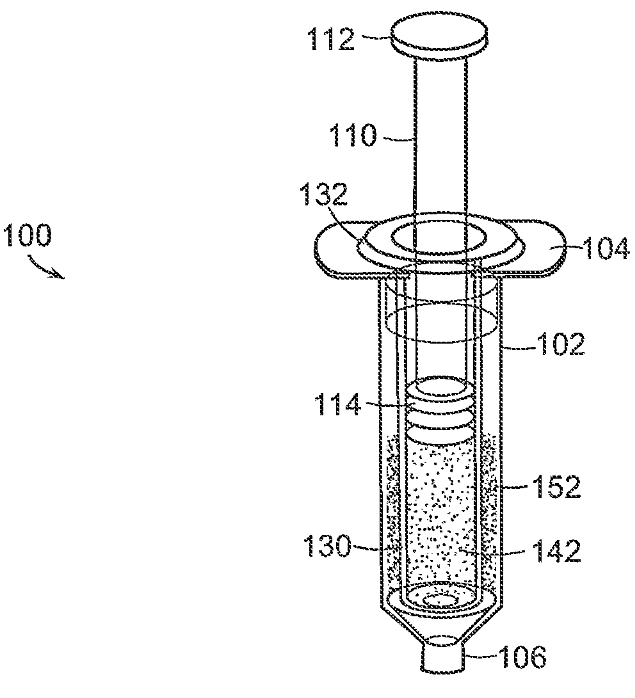
FIG. 1A is an isometric view of one embodiment of a multi-chamber syringe.

As described above, syringes may be used to deliver a material to a specified location. In some cases, multiple materials may be mixed prior to delivery. For example, many hemostatic agents include a dry component and a liquid component which may benefit from one or more mixing steps prior to use. Of course, syringes that deliver a mixture of multiple materials may be used in other areas outside of medicine. For example, syringes may be used in construction, manufacturing, and/or the hobby community, such as when applying a two-part epoxy. Accordingly, it should be appreciated that the present disclosure is not limited to any specific application.

Mixing multiple materials prior to delivery with a syringe may be associated with a number of challenges. First, a mixing process may include a complex sequence of steps that may be physically demanding, may require dexterity from the user, and/or may be difficult to perform. For example, some mixing procedures may require manually passing materials back and forth between two (or more)

syringes a large number of times to ensure adequate mixing and distribution. Additionally, a mixing process may be associated with long mixing times, which may delay use of the mixed materials. Delays due to mixing may be especially problematic during surgery, for example, when quick application of a hemostatic agent may be desired. Furthermore, a mixing process may result in clogging of a syringe or lumen if the mixing is not performed at an appropriate ratio, or in an appropriate amount of time. Adverse outcomes may additionally result from other variables related to the mixing process, including but not limited to specifics of the mixing environment (e.g., temperature, humidity, light), material properties (of the mixed materials and/or the container(s) in which they are mixed), and other variables.

In view of the above, the Inventors have recognized and appreciated the benefits of a multi-chamber syringe configured to enable mixing of multiple materials within the syringe itself. A multi-chamber syringe may be a "ready-to-use" option that reduces both the number of mixing steps as well as the mixing time compared to conventional mixing procedures. Furthermore, a multi-chamber syringe may be easier and more convenient to use compared to a conventional syringe. In addition, a multi-chamber syringe may reduce the amount of waste generated during a mixing procedure, as a single container may be used, compared to using multiple conventional chambers and potential additional mixing equipment.

In some embodiments, a multi-chamber syringe may include a syringe with multiple chambers, each of which may be configured to hold a different material. The chambers may be separated by one or more moveable barriers. Displacing a barrier that is located between two chambers may allow the materials disposed within those two chambers to mix. Additionally, the process of slidably displacing a barrier may generate turbulence in materials disposed in chambers adjacent the barrier, which may encourage more thorough mixing of the materials. In this way, a multi-chamber syringe with moveable barriers separating multiple chambers may be associated with a faster, simpler, and more consistent mixing of two or more materials within a solution as compared to conventional mixing procedures involving conventional syringes.

In one embodiment, a method of operating a multi-chamber syringe may include displacing a first plunger to draw a first material into a first chamber. Drawing a material into a chamber may include translating a plunger in a proximal direction along a longitudinal axis of the syringe. Without wishing to be bound by theory, displacing a plunger associated with a chamber of a syringe may increase a volume of the chamber, thereby generating a negative gauge pressure. This negative pressure may in turn draw in a material through an opening of the chamber, such as a nozzle of the syringe. After a first material is drawn into the chamber, a barrier disposed between the first chamber and a second chamber may be displaced to place the first and second chambers in fluid communication with one another and release a second material disposed in the second chamber. In some embodiments, the barrier may be displaced in the same direction as a first plunger. The first material and the second material may then mix together in a combined region of the first and second chambers of the syringe. As described further below, mixing may be encouraged as a barrier is displaced by generating turbulence within materials adjacent the barrier. In some instances, the first plunger associated with the first chamber, a second plunger associated with the second chamber, and the barrier may then be displaced with one another in a distal, or other appropriate, direction to dispense the mixed material from a nozzle of the syringe. In some embodiments, the barrier may be coupled to the first plunger and/or the second plunger prior to dispensing the mixed material.

In some embodiments, a multi-chamber syringe may include a plurality of chambers. It should be appreciated that a multi-chamber syringe may include two, three, four, five, or any suitable number of chambers, as the disclosure is not limited in this regard. Additionally, it should be appreciated that a chamber of a multi-chamber syringe may be of any suitable shape. A chamber of a multi-chamber syringe may be cylindrical, annular, prismatic, or any other suitable shape, as the disclosure is not limited in this regard. Relatedly, a cross-section of a chamber of a multi-chamber syringe taken perpendicular to a longitudinal axis of the syringe may be a circle, ellipse, oval, annulus, triangle, rectangle, or any other suitable shape as the disclosure is not limited to any particular chamber shape.

In some embodiments, a multi-chamber syringe may include a first chamber and a second chamber disposed in a nested arrangement in which the first chamber is disposed within the second chamber. For example, a first chamber may be substantially cylindrical, and may be arranged within a second chamber, which may be substantially annular. As such, the first chamber may be an interior chamber, while the second chamber may be an exterior chamber. The first and second chambers may be separated by a moveable barrier that may be annular or tubular. Two or more selected from the group of the first chamber, the barrier, the second chamber, and the syringe barrel may be concentric and/or co-axial. For example, in some embodiments, a barrier may be co-axial with a syringe barrel. In some embodiments, a barrier may be co-axial with a first plunger, and a first plunger may be at least partially disposed within a barrier. In some embodiments, a first plunger may be co-axial with a second plunger. Of course, a multi-chamber syringe with a nested arrangement of chambers may include more than two chambers, as the disclosure is not so limited. Additionally, a multi-chamber syringe may include nested chambers that may not be circular, annular, or otherwise radially symmetric. For example, a first chamber that includes a cross-section that is rectangular with rounded corners may be disposed within a second chamber that includes a cross-section that is an oval. It should be appreciated that a multi-chamber syringe with chambers in a nested arrangement may include chambers of any suitable shape, as the disclosure is not so limited.

In some embodiments, a multi-chamber syringe may include chambers arranged adjacent to each other such that they are not nested with one another. In embodiments with two chambers, a first chamber may be disposed adjacent to a second chamber. It should be appreciated that a multi-chamber syringe may include any suitable number of chambers of any suitable shape arranged adjacent to one another, as the disclosure is not limited in this regard. In some embodiments, a multi-chamber syringe may include a combination of nested and lateral arrangements of chambers. For example, a first chamber may be disposed adjacent a second chamber, both of which are disposed within a third chamber. A first planar barrier may separate the first and second chambers, while a second annular barrier may separate the first and second chambers from the third chamber.

In view of the above, it should be appreciated that a multi-chamber syringe may include any suitable number, shape, and arrangement of chambers, as the disclosure is not limited in this regard.

In some embodiments, a multi-chamber syringe may include one or more barriers disposed between the chambers of the syringe. The barriers may be moveable relative to the barrel of the syringe. Removing a barrier disposed between two chambers may allow materials disposed within those two chambers to mix, as the two chambers are no longer physically separated. In some embodiments, the act of displacing a barrier between chambers of a multi-chamber syringe may be associated with improved mixing of materials disposed within those chambers. Without wishing to be bound by theory, displacing a barrier may exert shear forces on one or more materials in contact with the barrier. Shear forces exerted on a fluid material may be associated with turbulence and/or turbulent mixing. Increased turbulence may be associated with increased mixing quality and/or decreased mixing times. Without wishing to be bound by theory, an amount of turbulence generated may be associated with a speed at which the barrier is removed, a fluid viscosity, a fluid density, a gap distance between the chamber walls and barrier, and/or additional variables relating to the barrier and/or the material(s) in contact with the barrier. In some embodiments, a barrier may include surface features configured to promote turbulent mixing, as described in greater detail below. It should be appreciated that, as used herein, the term "fluid" may refer to any state of matter with fluidic properties. Non-limiting examples include a liquid, a gas, a suspension, a gel, and/or a flowable solid (e.g., powder) each of which may be used with any of the embodiments described herein.

In some embodiments, a multi-chamber syringe may include one or more plungers configured to dispense a material out of a chamber and/or draw a material into a chamber. Each chamber of the syringe may be associated with a separate plunger. However, in some embodiments, a single plunger may be associated with multiple chambers, or multiple plungers may be associated with a single chamber, as the disclosure is not limited in regard to the relative number of chambers and plungers.

In some embodiments, plungers and/or barriers may be selectively engaged to lock together and form a plunger assembly. For example, after a barrier that separates a first chamber and a second chamber is slidably displaced to enable mixing of a first material and a second material, the barrier may be engaged with, and in some instances locked to, a first plunger and/or a second plunger to form a combined plunger. Depressing the combined plunger may dispense the mixed material from a combined volume of the first and second chambers. It should be appreciated that a combined plunger may include a combination of a plunger and a barrier, a combination of two plungers, a combination of a barrier and two plungers, or any other appropriate combination of any suitable number of plungers and/or barriers, as the disclosure is not limited in this regard. In some embodiments, a barrier and one or more plungers may be configured to lock with one another using a tab and slot, a friction fit, a magnetic coupling, a spring-loaded protrusion configured to be received in a recess, and/or any other suitable mechanism configured to enable coupling of a plunger and a barrier. It should be appreciated that any portion of a coupling may be disposed on either a barrier or a plunger. For example, in some embodiments, a barrier may include a tab, and a plunger may include a slot configured to receive the tab. In some embodiments, a plunger may include a tab, and a barrier may include a slot configured to receive the tab. Thus, the present disclosure is not limited in regards to the type of coupling or the specific arrangement of the coupling between a barrier and a plunger.

In some embodiments, a multi-chamber syringe may include one or more gaskets configured to provide a seal and prevent unwanted fluid communication between different areas of the syringe. One or more gaskets may be disposed between a first plunger and a barrier, between a barrier and a second plunger, between a second plunger and a barrel, between a barrier and an internal wall of one or more chambers, or between any other appropriate components of a multi-chamber syringe, as the disclosure is not so limited. For example, an O-ring may be disposed between a barrier and a plunger. However, it should be appreciated that a gasket may include any suitable material of any suitable shape configured to make a seal, as the disclosure is not limited in this regard. In some embodiments, different surfaces of components of a multi-chamber syringe may include coatings and/or strips of material configured to promote sealing between different chambers. For instance, a plunger head may include an elastomeric material, such as a rubber, configured to make a water-tight seal when disposed adjacent to another surface. Additionally or alternatively, a surface may include an elastomeric coating configured to promote a seal when a plunger and/or a barrier contacts the surface. For example, a distal interior surface of one or more portions the barrel may include an elastomeric material configured to create a seal when a barrier is in contact with the seal.

In some embodiments, a material may be disposed within one or more chambers of a multi-chamber syringe. A material may include any suitable material of any suitable form, as the disclosure is not limited in this regard. A material may be a solid, liquid, gas, gel, suspension, or may be in any other suitable form. A single chamber may include multiple materials, such as a mixture of two liquid materials, or a solid material suspended in a liquid material. As such, mixing materials from different chambers of a multi-chamber syringe (such as when removing a barrier) may include mixing solids, liquids, gasses, or any other form of material. The resulting mixed material may similarly be a solid, liquid, gas, suspension, gel, flowable matrix, or any suitable form of material.

In some embodiments, the first and/or second materials may include a therapeutic compound, a carrier such as saline, and/or any other appropriate material. Therapeutic compound may include, but are not limited to, thrombin, a hemostat, combinations of the forgoing, and/or any other appropriate agent. For example, a first material in a first chamber may include saline, or a mixture of saline and thrombin, and a second material in a second chamber may include a hemostat, such as collagen. The hemostat may be in the form of powder, sheets, and/or fabrics. In some embodiments, a material may at least partially include dextran. However, it should be appreciated that any suitable material may be contained in any chamber of a multi-chamber syringe, as the disclosure is not limited in this regard.

Therapeutic compounds for purposes of this application may correspond to any appropriate material including, but not limited to, any drug, medication, pharmaceutical preparation, contrast agent, and/or biologic such as a protein, antisense molecule, and gene therapy viral vector as the disclosure is not so limited. When a therapeutic compound is present in a particular location in an "effective amount" it means a concentration of the therapeutic compound is greater than or equal to a trace amount and is sufficient for achieving a desired purpose, such as, for example, to permit detection of the therapeutic compound in a subject for diagnostic purposes, to treat a disease or condition in a subject, and/or enhance a treatment of a disease or condition in a subject. In some embodiments, an effective amount of a particular therapeutic compound is present in an amount sufficient to reduce or alleviate one or more conditions associated with a particular condition.

In some embodiments, a multi-chamber syringe may include one or more protrusions and/or surface features configured to promote mixing. As described above, slidably displacing a barrier may be associated with generating turbulence within a fluid material adjacent the barrier. Protrusions and/or surface features on a moveable barrier (or any other component of a multi-chamber syringe) may be configured to increase the amount of turbulence produced. Protrusions and/or surface features may include fins, recessions, dimples, ribs, or any other suitable protrusion and/or surface feature, as the disclosure is not limited in this regard. A protrusion and/or surface feature may be disposed on any suitable component and/or surface of a multi-chamber syringe, including but not limited to a barrier, a plunger, a barrel, a nozzle, and/or a barrel tip. For example, a distal portion of a barrier may include one or more mixing fins configured to generate turbulent mixing as the barrier is displaced relative to materials disposed in chambers adjacent the barrier. It should be appreciated that protrusions and/or surface features may promote mixing without generating turbulence, as the disclosure is not limited in this regard.

In some embodiments, a multi-chamber syringe may include one or more functional coatings on any appropriate surface of the syringe to provide various desired functionalities. For example, a coating may be disposed on an inner surface of a barrel, an out surface of a barrier, and/or any other suitable surface of the syringe. In some embodiments, a coating may include a hydrophobic coating. A hydrophobic coating may help to improve mixing of one or more materials disposed within the syringe when a barrier between two chambers containing different materials is removed. Without wishing to be bound by theory, a hydrophobic coating may discourage a material disposed within a chamber from adhering to a surface of the chamber, thereby enabling the production of a more homogeneous mixture. Of course, other coatings may be included in a multi-chamber syringe in addition, or as an alternative, to a hydrophobic coating. Accordingly, it should be appreciated that any suitable coatings may be included on any suitable surface of any suitable portion of a multi-chamber syringe, as the disclosure is not so limited.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1A is an isometric view of one embodiment of a multi-chamber syringe 100. The syringe 100 includes a housing and a first plunger 110 disposed at least partially within an internal cavity of the housing. In the embodiment of the figure, the housing is a barrel 102 of the syringe 100. The first plunger 110 is slidably displaceable relative to the barrel 102. A proximal portion of the barrel 102 includes a barrel flange 104. In some embodiments, a barrel flange may assist a user in grasping and/or manipulating a syringe. For example, a barrel flange may be configured to receive or be grasped by one or more fingers of a user's hand when the user operates a syringe. In the embodiment of the figure, a distal portion of the barrel 102 includes a nozzle 106 or other appropriate outlet. In some embodiments, displacing one or more plungers relative to a housing of a syringe may dispense a material disposed within the housing out of the nozzle. In the embodiment of the figure, a proximal portion of the first plunger 110 includes a first plunger flange 112. In some embodiments, a plunger flange may assist a user in grasping and/or manipulating a position of the plunger within the syringe. For example, a plunger flange may be configured to receive a thumb of a user's hand when the user operates a syringe. In the embodiment of the figure, a distal portion of the first plunger 110 includes a first plunger head 114. A plunger head may include one or more elastomeric portions, a gasket, an O-ring, or any other suitable structure configured to provide a seal between the plunger head and a body in which the plunger head may be disposed to form a sliding seal there with.

The multi-chamber syringe 100 additionally includes a barrier 130 disposed at least partially within the internal cavity of the barrel 102. The barrier 130 is slidably displaceable relative to both the barrel 102 and first plunger 110 in a distal direction along a longitudinal axis of the syringe 100. However, embodiments in which the barrier is moveable in a different direction are also contemplated. A proximal portion of the barrier 130 may include a barrier flange 132. In some embodiments, a barrier flange may assist a user in grasping and/or manipulating syringe position of the barrier within the syringe.

Figure 1B:
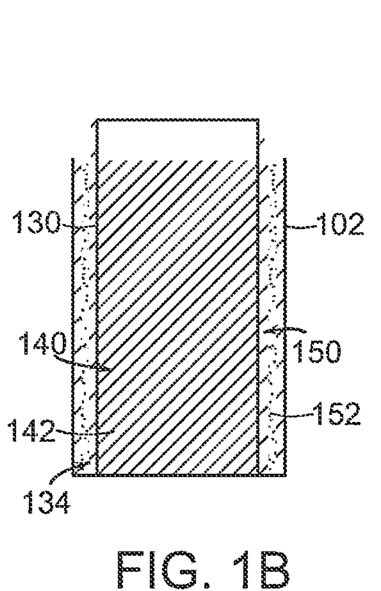
FIG. 1B is a front schematic view of a barrel of the multi-chamber syringe of FIG. 1A before a barrier is displaced.
Figure 1C:
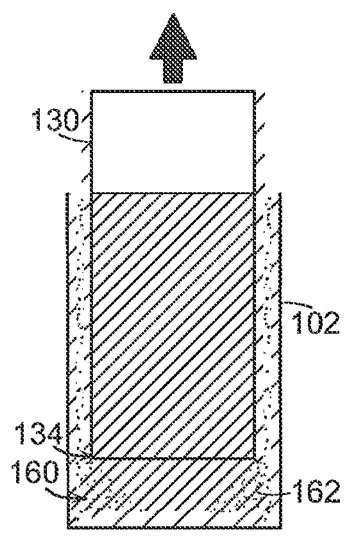
FIG. 1C is a front schematic view of the barrel of the multi-chamber syringe of FIG. 1A after a barrier has been displaced.

FIGS. 1B and 1C are schematics of the multi-chamber syringe 100 of FIG. 1A before and after (respectively) the barrier 130 is displaced. When the barrier 130 is in an initial sealed configuration, as shown in FIG. 1B, a distal portion 134 of the barrier 130 may contact a distal interior surface, or other appropriate interior surface, of the barrel 102 to form a seal. As noted above, the barrier may be displaced in a proximal direction along a longitudinal axis of the syringe to move the barrier to an unsealed configuration. In this way, the barrier 130 is configured to selectively separate different chambers of the internal cavity. That is, the barrier 130 partially defines first and second chambers within the internal cavity of barrel 102. A first chamber 140 is bounded at least in part by an interior surface of the barrier 130, a distal surface of the barrel 102, and a distal surface of the first plunger 110, such as a surface of the first plunger head 114. Correspondingly, a second chamber 150 is bounded at least in part by an exterior surface of the barrier 130, a distal surface of the barrel 102, an interior surface of the barrel 102, and a distal surface of a second plunger (not shown for clarity). A first material 142 is disposed in the first chamber 140, and a second material 152 is disposed in the second chamber 150. As shown in FIG. 1C, as the barrier 130 is retracted in the proximal direction relative to the internal cavity of the barrel, the distal portion 134 of the barrier 130 breaks contact with the distal interior surface of the barrel 102, thereby breaking the seal. Consequently, the first chamber 140 and the second chamber 150 are placed in fluid communication with one another to form a combined volume, thereby allowing the first material 142 and the second material 152 to mix into a mixed material 162 in a combined volume 160 as the barrier is displaced towards a fully displaced configuration.

Figures 2A, 2B, 2C:
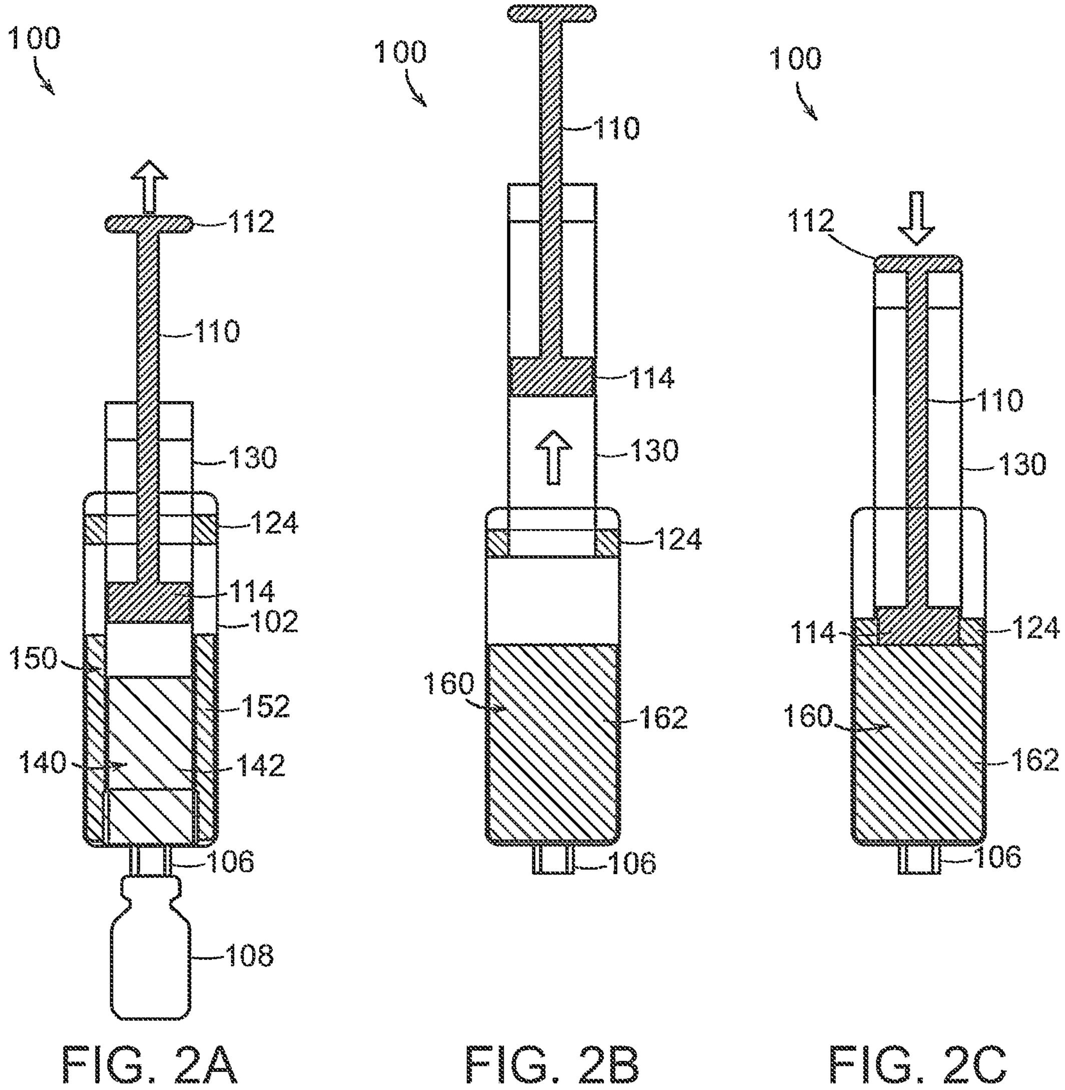
FIG. 2A is a front view of one embodiment of a multi-chamber syringe as a first material is drawn into a first chamber by displacing a first plunger.
FIG. 2B is a front view of the multi-chamber syringe of FIG. 2A after a barrier is displaced to enable mixing of the first material and a second material.
FIG. 2C is a front view of the multi-chamber syringe of FIG. 2A as the first plunger and a second plunger are displaced together to dispense the mixed first and second materials from the syringe.

FIGS. 2A-2C depict one embodiment of a mixing sequence involving a multi-chamber syringe 100. The syringe 100 includes a barrel 102 which includes a nozzle 106 or other outlet. The nozzle 106 of the barrel 102 is coupled to a vial 108. As seen in FIG. 2A, retracting a first plunger 110 of the syringe 100 draws a first material 142 from the vial 108 through the nozzle 106 and into a first chamber 140 within the barrel 102 of the syringe 100. A second material 152 is disposed in a second chamber 150. The first plunger 110 includes a first plunger flange 112 configured to be grasped by a user when drawing in the first material 142 from the vial 108. As seen in FIG. 2B, a barrier 130 of the syringe 100 may be displaced relative to the barrel 102. As the barrier 130 is displaced, the first material 142 mixes with the second material 152 to form a mixed material 162 in a combined region 160. As the barrier 130 is displaced, the first plunger 110 is displaced along with the barrier 130, such that a first plunger head 114 does not move relative to the barrier 130. In other embodiments, displacing a barrier may include displacing a barrier relative to a housing of a syringe, one or more plungers of a syringe, or any other portion of a syringe. As seen in FIG. 2C, the first syringe 110 is displaced relative to the barrier 130. Eventually, the first plunger 110 reaches a fully deployed position relative to the barrier 130. At this point, the first plunger head 114 is aligned with a second plunger head 124 of a second plunger (not shown) associated with the second chamber 150. The first plunger 110, the barrier 130, and the second plunger form a combined plunger. Displacing the combined plunger dispenses the mixed material 162 out of the combined volume 160 through the nozzle 106.

Figure 3:
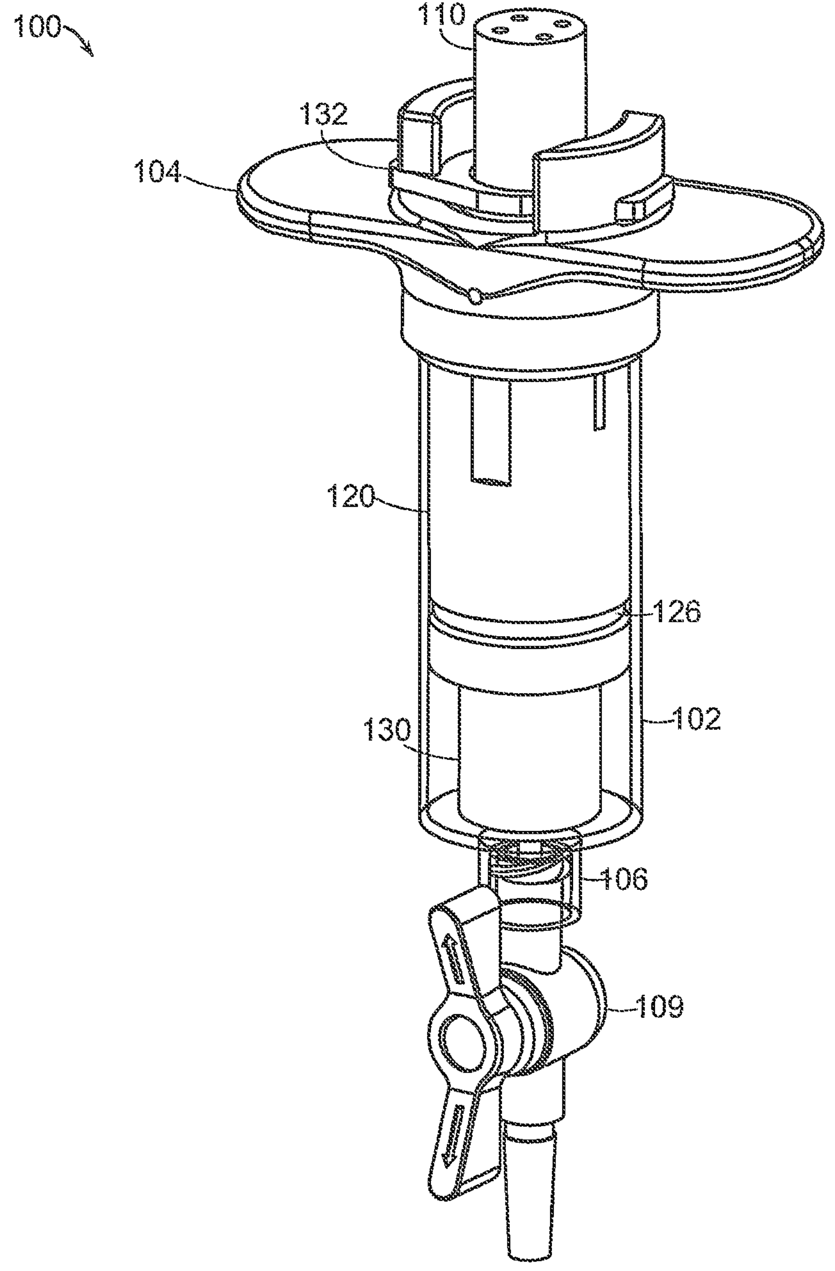
FIG. 3 is a perspective view of one embodiment of a multi-chamber syringe.
Figure 4:
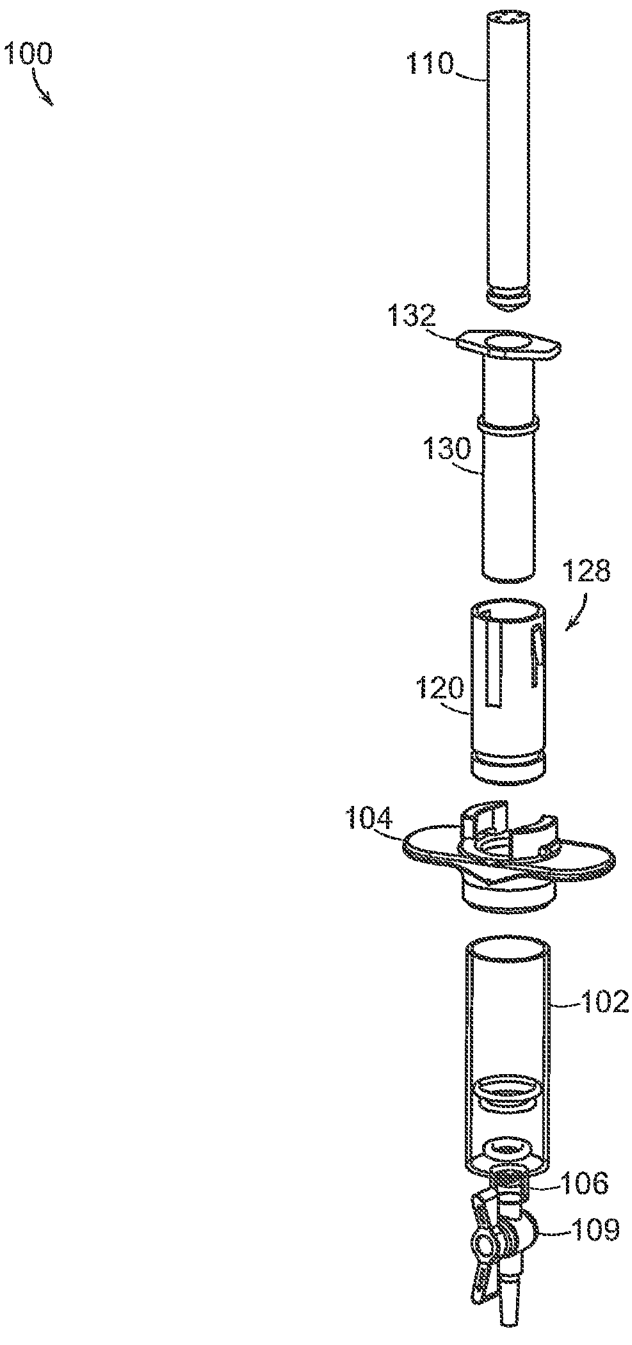
FIG. 4 is an exploded perspective view of one embodiment of a multi-chamber syringe.
Figure 5:
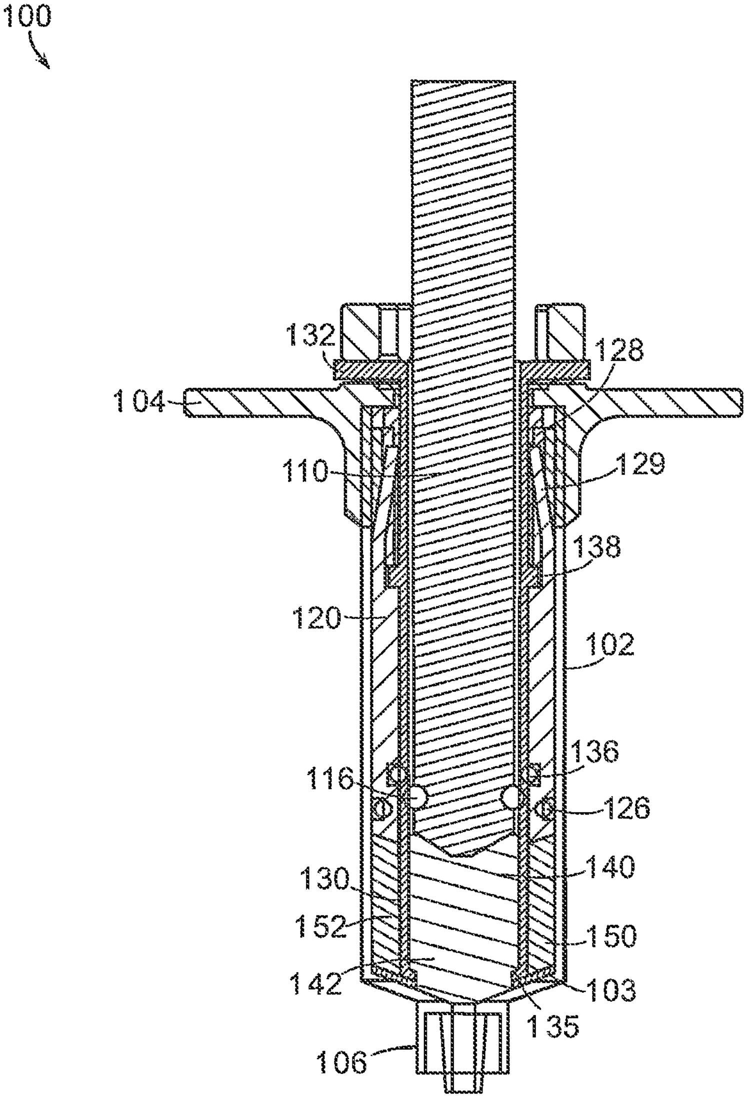
FIG. 5 is a front cross-sectional view of one embodiment of a multi-chamber syringe.

FIGS. 3-5 depict various views of one embodiment of a multi-chamber syringe 100. The syringe 100 includes a barrel 102 with an internal volume. A distal portion of the barrel 102 includes a nozzle 106 or other outlet in fluid communication with the internal volume of the barrel, and a proximal portion of the barrel 102 may include a barrel flange 104. A first plunger 110 is disposed at least partially within an internal cavity of the barrel 102, and is slidably displaceable relative to the barrel 102. In addition, a second plunger 120 is disposed at least partially within an internal cavity of the barrel 102, and is slidably displaceable relative to the barrel 102. In the depicted embodiment, the second plunger is disposed at least partially around the first plunger. A barrier 130 is disposed at least partially between the first plunger 110 and the second plunger 120. As shown in the figure, in some embodiments, the barrier may be a tube that disposed between and coaxially located with the first and second plungers. Again, the barrier may form first and second chambers within the barrel via a seal formed between a distal portion of the barrier and a distal interior surface of the barrel with which the distal portion of the barrier is in contact. In some embodiments, the distal interior surface of the barrel may include a coating 103 such as an elastomeric coating to aid with sealing of the barrier.

The first plunger 110 and the second plunger 120 may be disposed in the regions of the internal volume of the barrel 102 corresponding to the first and second chambers 140 and 150 respectively such that movement of the plungers may alter the volume included in the first and second chambers. In either case, the barrier may be slidably displaceable relative to the first plunger 110, the second plunger 120, and the barrel to selectively isolate or place the first and second chambers in fluid communication with one another. As best shown in FIG. 5, the first chamber 140 is in fluid communication with the nozzle 106 or other outlet of the syringe 100. Thus, proximal movement of the first plunger 110 relative to the barrier while it is in the initial sealed configuration may draw a first material 142 into the first chamber. However, embodiments in which a first material is already contained in the first chamber are also contemplated. Additionally, in an initial configuration, the second plunger 120 may be distanced from a distal interior surface of the barrel to define an initial volume for the second chamber 150 which may contain a second material 152 disposed therein. Until the barrier is displaced to the unsealed configuration, the second volume may be isolated from the nozzle of the syringe. Operation of these components is elaborated on below.

In some embodiments, the first plunger, barrier, and second plunger may be configured to be independently displaceable along a longitudinal axis of the syringe relative to one another in a first mode of operation and together in unison with one another in a second mode of operation as detailed further below. For example, in one embodiment, a barrier may be selectively engageable with one or more plungers of a multi-chamber syringe to move the plungers and barrier of the syringe in unison when dispensing material from the syringe. In the embodiment of the figure, the barrier 130 includes a locking structure such as one or more tabs 138 configured to engage with slots 128 or another appropriate structure of the second plunger 120 when the barrier is moved proximally relative to the second plunger towards the unsealed configuration. Specifically, displacing the barrier 130 in a proximal direction translates the tabs 138 in a proximal direction towards the slots 128 of the second plunger 120. After translating a predetermined distance, the tabs 138 engage with the slots 128, thereby coupling the barrier 130 with the outer plunger 120. One or more flat springs 129 are configured to lock the tabs 138 into the slots 128. Thus, in some embodiments, a barrier may be configured to engage with a plunger to couple the barrier and one or more of the plungers such that they may move in unison with one another in a distal direction along a longitudinal axis of the syringe when dispensing material from the syringe. Of course, while a particular lock has been shown to couple a barrier and a plunger, the disclosure is not limited to the depicted tabs and slots. Thus, any appropriate locking arrangement may be used as previously noted. Additionally, embodiments in which the barrier and one or more of the plungers are not locked together once in the unsealed configuration are also contemplated.

In some instances, it may be desirable to avoid unintended movement of a barrier from a sealed to an unsealed configuration. Thus, in some embodiments, a barrier 130 may include a barrier flange 132 disposed in a recess of the barrel 102 proximal to the barrel flange 104. Rotating the barrier 130 about a longitudinal axis releases the barrier flange 132 from the recess of the barrel 102, thereby freeing the barrier to translate along the longitudinal axis. However, any appropriate lock including latches, detents, pins, or other arrangement may also be used to prevent unintentional displacement of a barrier.

To provide the desired sealing, a multi-chamber syringe 100 may include a number of gaskets. As shown in the figures, the first plunger 110 includes a circumferential recess located on a distal portion of the first plunger. The recess is configured to receive a first plunger gasket 116 disposed between the first plunger 110 and the barrier 130. The second plunger 120 includes a first circumferential recess disposed on an exterior surface of the second plunger that is configured to receive a second plunger gasket 126 disposed between the second plunger 120 and the barrel 102. Additionally, the second plunger 120 includes a second circumferential recess disposed on an interior surface of the second plunger that is configured to receive a barrier gasket 136 disposed between the second plunger 120 and the barrier 130. These gaskets may permit the plungers and barrier to move relative to each other while maintaining the desired seals with one another. As described above, a gasket may be any suitable material, size, or shape configured to provide a seal as the disclosure is not limited to the specific type of gasket or seal used in the disclosed embodiments.

Figures 6A, 6B, 6C:
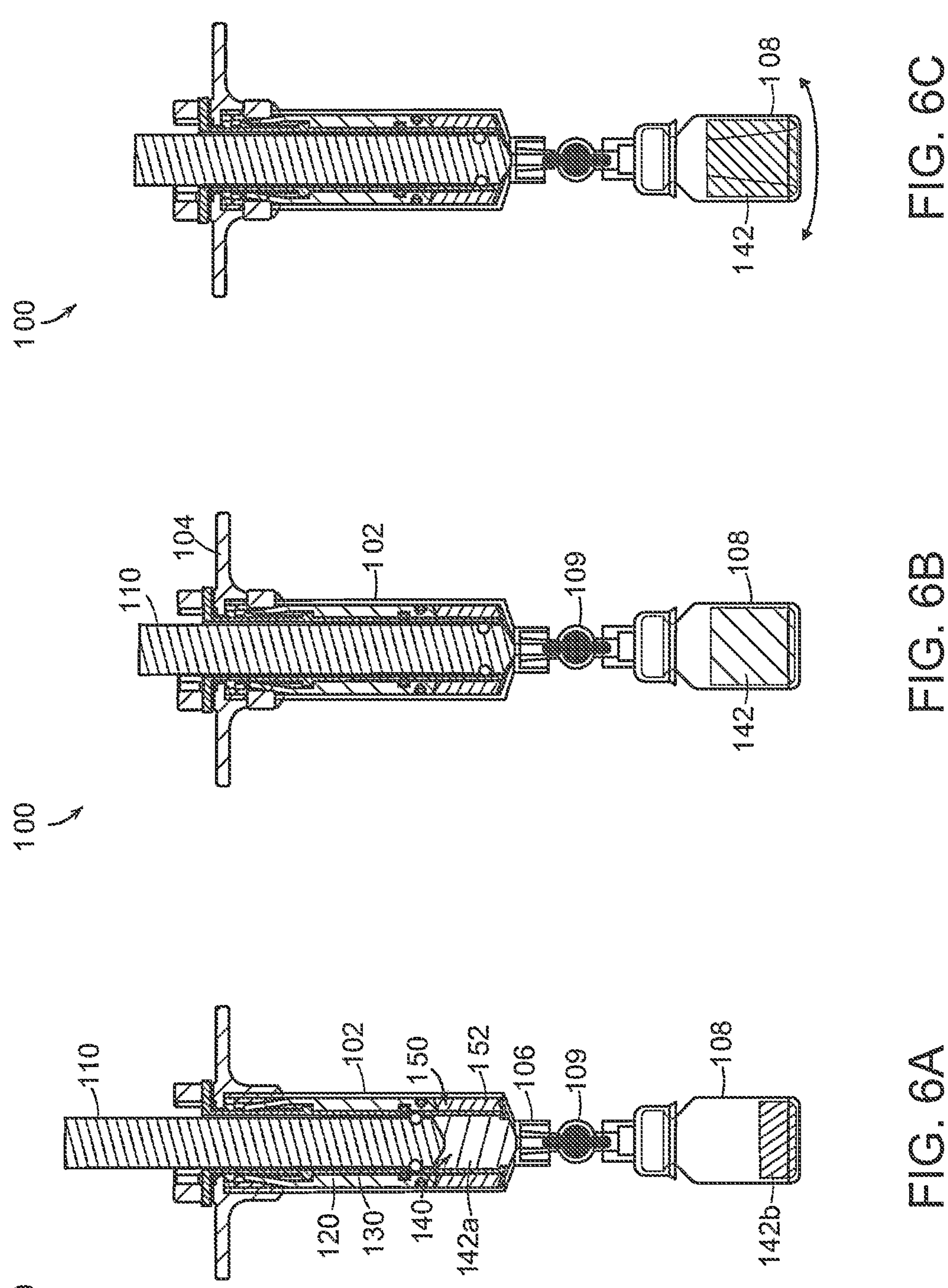
FIGS. 6A-6I depict one embodiment of a method of operating a multi-chamber syringe.

FIGS. 6A-6I depict one embodiment of a method of using a multi-chamber syringe similar to that described in relation to FIGS. 3-5. In FIG. 6A, a multi-chamber syringe 100 is coupled to a vial 108 through a valve 109 in fluid communication with a nozzle 106 of a barrel 102 of the syringe 100. As detailed above, the barrel 102 includes an internal cavity, disposed in which are a first plunger 110, a second plunger 120, and a barrier 130. A first chamber 140 is disposed within the internal cavity of the barrier and is associated with the first plunger, and a second chamber 150 is disposed between the barrier and an interior surface of the barrier and is associated with the second plunger. A first part of a first material 142*a* is disposed within the first chamber in an initial state. A second material 152 is disposed within the second chamber. Disposed within the vial 108 is a second part of the first material 142*b*. In some embodiments, the vial may contain thrombin and the first chamber may initially contain saline. In some embodiments, the second chamber may contain dextran, a starch-based material, and/or a collagen-based material. It should be appreciated that any suitable material may be disposed in any chamber of a syringe and/or a vial.

In FIG. 6B, the first plunger 110 is displaced distally relative to the barrel 102. The barrel 102 includes a barrel flange 104 configured to assist a user in displacing the first plunger 110. As the first plunger is displaced, the first part of the first material 142*a* is dispensed out of the first chamber 140, through the nozzle 106, through the open valve 109, and into the vial 108. The first part of the first material 142*a* mixes with the second part of the first material 142*b*, resulting in a first material 142. In FIG. 6C, the vial 108 may be shaken to promote further mixing. In some embodiments, saline may be injected into a vial containing thrombin (or any other suitable therapeutic fluid), and shaking a vial may include swirling a vial to reconstitute the thrombin (or other fluid).

Figure 6F:
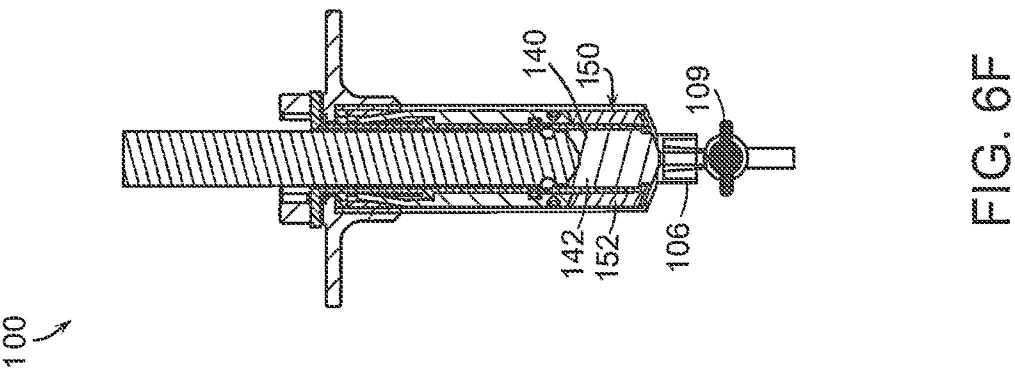
Figure 6E:
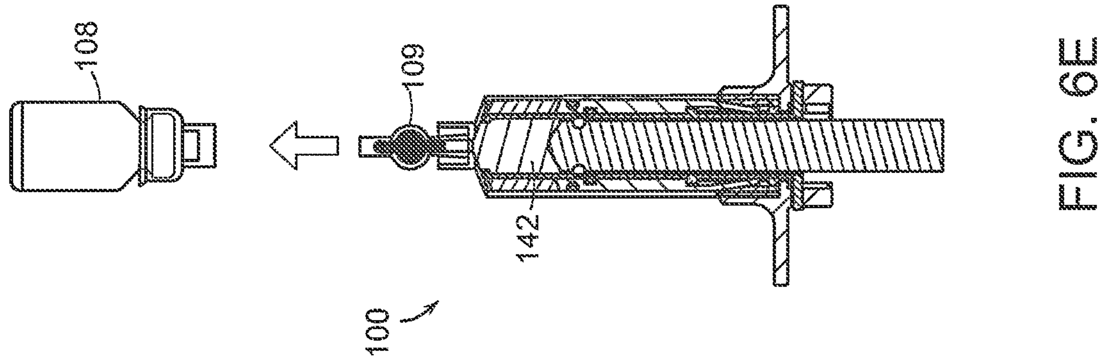
Figure 6D:
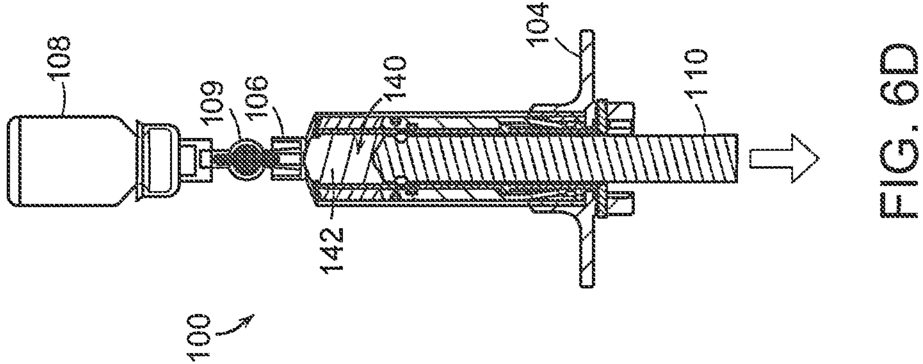

In FIG. 6D, the first plunger 110 is retracted to draw the first material 142 out of the vial 108 and into the first chamber 140. In FIG. 6E, the vial 108 is decoupled from the syringe 100. In FIG. 6F, the valve 109 is closed, thereby preventing material from exiting the nozzle 106 of the syringe 100. In some embodiments, a material drawn into the syringe may include a mixture of saline and thrombin, although other materials and/or combinations of materials are contemplated, and the disclosure is not limited in this regard. It should be appreciated that in some embodiments of a method of operating a multi-chamber syringe, the steps depicted in FIGS. 6A-6E may not be included. That is, in some embodiments, a method may begin with a syringe in the state depicted in FIG. 6F, wherein the syringe includes two or more chambers holding two or more materials that are ready to be mixed.

Figures 6G, 6H, 6I:
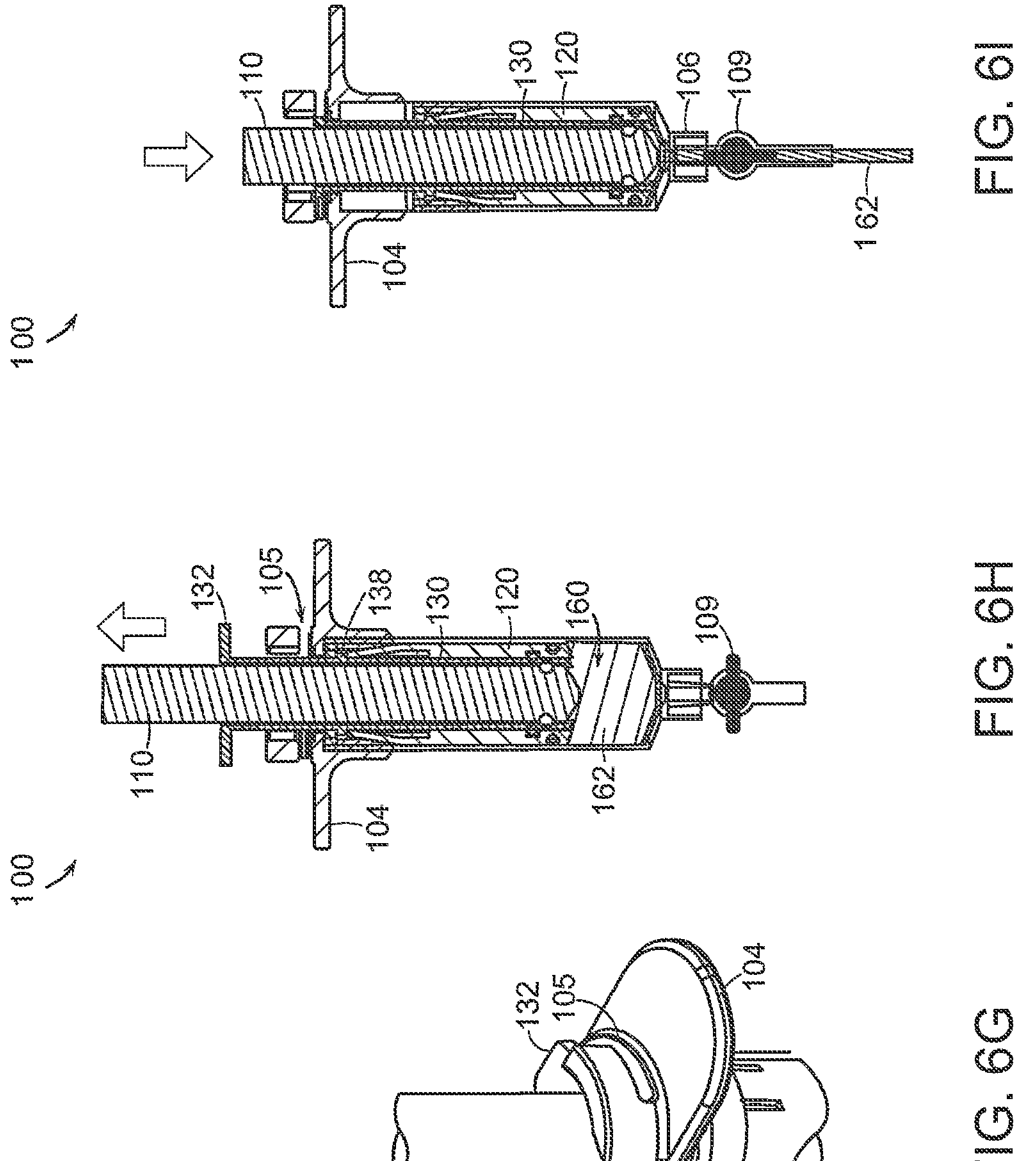

In FIG. 6G, a barrier flange 132 formed in a proximal portion of the barrier 130 may be rotated out of a recess 105 of the barrel flange 104. After the barrier flange 132 is released from the recess 105, the barrier 130 is unlocked from the barrel 102 of the syringe 100 and is free to translate in an axial direction. Although a tab and slot configuration is shown in the embodiment of FIG. 6G, it should be appreciated that the disclosure is not limited to couplings of this type. Rather, any suitable releasable coupling between a barrier and a syringe body may be used, including but not limited to a tab and slot, a friction fit, a magnetic coupling, a spring-loaded protrusion configured to be received in a recess, and/or any other suitable mechanism configured to selectively permit or prevent movement of the barrier. In FIG. 6H, the barrier 130 is slidably displaced in a proximal direction until tabs 138 of the barrier 130 engage with slots 128 of the second plunger 120, thereby coupling the barrier 130 and the second plunger 120 such that the barrier and second plunger may move in unison with one another during distal displacement of the combined plunger assembly. Without a distal portion of the barrier 130 contacting a distal interior surface of the barrel 102, the first chamber 140 and the second chamber 150 are no longer separated, thereby allowing the first material 142 and the second material 152 to mix in a combined volume 160 to yield a mixed material 162.

In FIG. 6I, the valve 109 is opened, and the first plunger 110 is displaced in a distal direction. In the depicted embodiment, the barrier 130 includes a lip 135 that extends radially inwards to engage with a distal surface of the first plunger. Thus, distal movement of the first plunger correspondingly displaces the barrier in the distal direction. Due to the tabs 138 of the barrier 130 being engaged with the slots 128 of the second plunger 120, the second plunger 120 is also displaced in the distal direction as the barrier is displaced. In this way, the first plunger 110, the barrier 130, and the second plunger 120 form a combined plunger configured to displace the mixed material 162 from the combined volume 160. As the combined plunger is displaced, the mixed material 162 is dispensed out of the combined volume 160, through the nozzle 106, and out of the open valve 109, thereby delivering the mixed material 162 to a targeted location. In some embodiments, the distal portions of the plungers and barrier may be shaped to form a surface that substantially matches a size and shape of the distal interior surface of the barrel. Of course, while a particular construction for forming a combined plunger from a barrier and two plungers has been depicted, it should be understood that any appropriate construction capable of functioning as a combined plunger for dispensing material from the syringe may be used.

FIGS. 7A-7C show various embodiments of protrusions of a multi-chamber syringe configured to promote mixing. In the embodiments of the figures, protrusions 170 and 172 are disposed on an interior and/or exterior surface of a barrier 130 (shown in a top cross-sectional view). The barrier 130 is disposed within an internal cavity of a barrel 102 of a syringe. As described above, protrusions and/or surface features such as fins, recessions, dimples, or ribs may be configured to promote turbulent mixing of materials within a multi-chamber syringe. A protrusion and/or surface feature may be disposed on any suitable component and/or surface of a multi-chamber syringe, including but not limited to a barrier, a plunger, a barrel, and/or a barrel nozzle. In the embodiments of the figures, the barrier 130 includes both protrusions 170 that project into a first chamber 140 adjacent the barrier 130 as well as protrusions 172 that project into a second chamber 150 adjacent the barrier 130. As the barrier 130 is displaced relative to materials disposed in the first and second chambers 140 and 150, projections 170 and 172 may promote turbulence, thereby enhancing the mixing between the materials.

FIGS. 8A-8E depict one embodiment of a multi-chamber syringe 100 with a combined plunger 180. The combined plunger 180 may be configured to manipulate material disposed in a plurality of chambers of a multi-chamber syringe. The combined plunger 180 may include one or more features configured to accept a barrier 130. In this way, a combined plunger 180 and a barrier 130 may form a nested and/or interlocking structure when both the combined plunger 180 and the barrier 130 are in the same relative position (e.g., fully retracted or fully deployed).

Figures 8A, 8B, 8C:
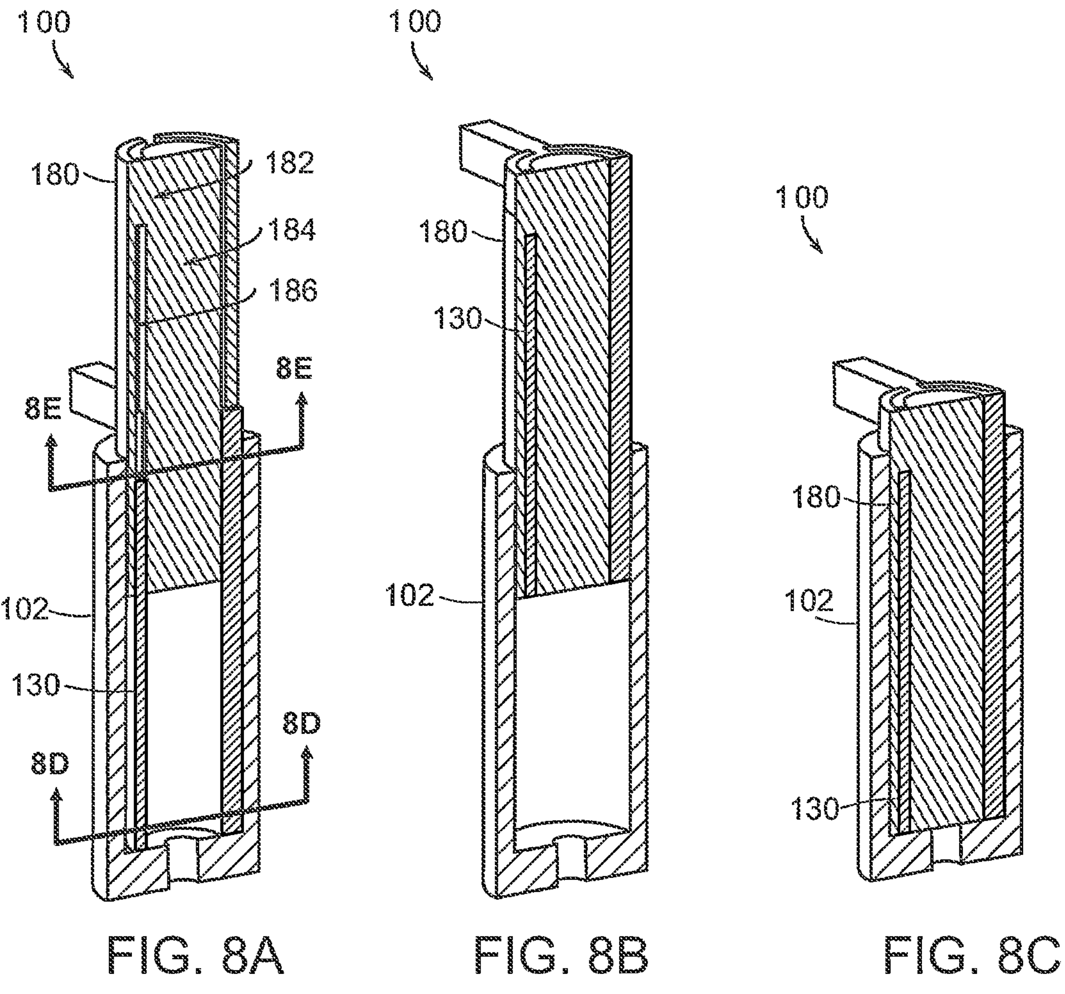
FIGS. 8A-8E depict one embodiment of a multi-chamber syringe with a combined plunger.

FIG. 8A shows a cross-sectional side view of the multi-chamber syringe 100 with the barrier 130 deployed and the combined plunger 180 retracted. The combined plunger 180 may include a connection portion 182 that connects an internal portion 184 and an external portion 186 of the combined plunger 180. An internal portion 184 of the combined plunger 180 may be associated with an internal chamber of the multi-chamber syringe 100. An external portion 186 of the combined plunger 180 may be associated with an external chamber of the multi-chamber syringe 100. Of course, it should be appreciated that a combined plunger 180 may include any suitable shape and/or arrangement of portions, which may depend at least in part on the corresponding shapes and/or arrangements of a multi-chamber syringe.

Figures 8D, 8E:
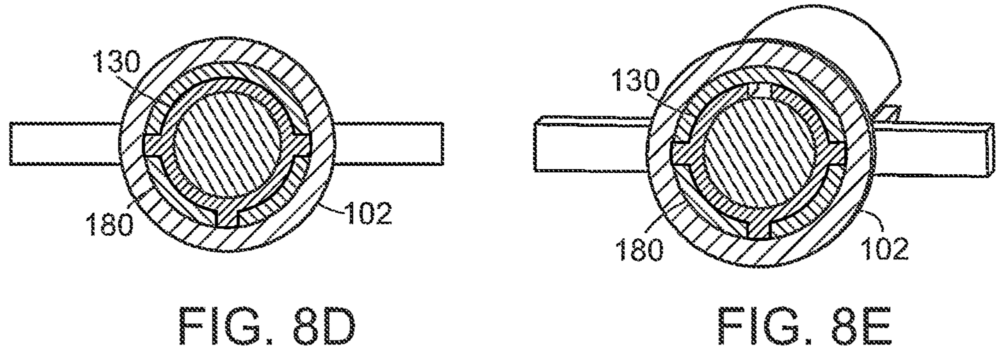

In FIG. 8B, when the barrier 130 is displaced relative to the barrel 102, the barrier 130 retracts into recesses within the combined plunger 180, forming an interlocking structure. FIG. 8C shows the interlocking structure of the combined plunger 180 and the barrier 130 in a deployed position. An interlocking structure may allow for rapid depression and/or dispensing of a material from the syringe 100. FIGS. 8D-8E depict cross-sectional bottom views of the multi-chamber syringe, as indicated in FIG. 8A. These views help elucidate the structural features that allow the combined plunger 180 to be disposed on both interior and exterior sides of the barrier 130.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A multi-chamber syringe comprising:

a housing including an internal cavity;

a first plunger disposed at least partially within the internal cavity of the housing, wherein the first plunger is slidably displaceable relative to the housing;

a second plunger disposed at least partially within the internal cavity of the housing, wherein the second plunger is slidably displaceable relative to the housing; and a barrier disposed at least partially between the first plunger and the second plunger within the internal cavity of the housing, wherein the barrier is slidably displaceable relative to the first plunger and the second plunger, wherein the first plunger and the barrier are each configured to be independently displaceable relative to one another and the second plunger in a first mode of operation, and wherein the first plunger, the second plunger, and the barrier are configured to move in unison in a second mode of operation.

2. The multi-chamber syringe of claim 1, wherein the barrier is selectively engageable with the first plunger and/or the second plunger.

3. The multi-chamber syringe of claim 1, further comprising a first material disposed in a first chamber bounded at least in part by a first surface of the barrier and a distal surface of the first plunger.

4. The multi-chamber syringe of claim 3, wherein the first material comprises saline.

5. The multi-chamber syringe of claim 1, further comprising a second material disposed in a second chamber bounded at least in part by a second surface of the barrier and a distal surface of the second plunger.

6. The multi-chamber syringe of claim 5, wherein the second material comprises one or more selected from a group comprising dextran, a starch-based material, and a collagen-based material.

7. The multi-chamber syringe of claim 1, wherein the housing is annular, and wherein the barrier is annular.

8. The multi-chamber syringe of claim 7, wherein the barrier is co-axial with the housing.

9. The multi-chamber syringe of claim 1, wherein the first plunger is cylindrical.

10. The multi-chamber syringe of claim 9, wherein the barrier is annular, and wherein the barrier is co-axial with the first plunger.

11. The multi-chamber syringe of claim 9, wherein the second plunger is annular.

12. The multi-chamber syringe of claim 11, wherein the second plunger is co-axial with the first plunger.

13. The multi-chamber syringe of claim 1, further comprising one or more gaskets between two or more selected from the group of the first plunger, the barrier, the second plunger, and the housing.

14. The multi-chamber syringe of claim 1, wherein the barrier is configured to lock with the first plunger and/or the second plunger when displaced to an unsealed configuration.

15. The multi-chamber syringe of claim 1, further comprising one or more protrusions formed on the barrier, wherein the protrusions are configured to promote mixing.

16. A multi-chamber syringe comprising:

a housing including an internal cavity;

a first plunger disposed at least partially within the internal cavity of the housing, wherein the first plunger is slidably displaceable relative to the housing;

a second plunger disposed at least partially within the internal cavity of the housing, wherein the second plunger is slidably displaceable relative to the housing; and a barrier disposed at least partially between the first plunger and the second plunger within the internal cavity of the housing such that the barrier is co-axial with the first and second plungers and the second plunger is positioned radially outward relative to the barrier about a longitudinal axis of the syringe, wherein the barrier forms a first chamber bounded by at least a first surface of the barrier and a distal surface of the first plunger and a second chamber bounded by at least a second surface of the barrier and the distal surface of the second plunger, and wherein the barrier is slidably displaceable relative to the first plunger and the second plunger to facilitate mixing between volumes of the first and second chambers.

17. The multi-chamber syringe of claim 16, further comprising a first material disposed in the first chamber and a second material disposed in the second chamber.

18. The multi-chamber syringe of claim 17, wherein the first material comprises saline, and wherein the second material comprises one or more selected from a group comprising dextran, a starch-based material, and a collagen-based material.

19. The multi-chamber syringe of claim 16, wherein the barrier is configured to lock with the first plunger and/or the second plunger when displaced to an unsealed configuration.

20. The multi-chamber syringe of claim 16, wherein the housing is annular and the barrier is annular, and wherein the barrier is co-axial with the housing.

21. A multi-chamber syringe comprising:

a housing including an internal cavity;

a first plunger disposed at least partially within the internal cavity of the housing, wherein the first plunger is slidably displaceable relative to the housing;

a second plunger disposed at least partially within the internal cavity of the housing, wherein the second plunger is slidably displaceable relative to the housing; and a barrier disposed at least partially between the first plunger and the second plunger within the internal cavity of the housing, wherein the barrier forms a first chamber bounded by at least a first surface of the barrier and a distal surface of the first plunger and a second chamber bounded by at least a second surface of the barrier and the distal surface of the second plunger, and wherein the barrier is slidably displaceable relative to the first plunger and the second plunger to facilitate mixing between volumes of the first and second chambers, and wherein the barrier is configured to lock with the first plunger and/or the second plunger when displaced to an unsealed configuration.

22. The multi-chamber syringe of claim 21, further comprising a first material disposed in the first chamber and a second material disposed in the second chamber.

23. The multi-chamber syringe of claim 22, wherein the first material comprises saline, and wherein the second material comprises one or more selected from a group comprising dextran, a starch-based material, and a collagen-based material.

24. The multi-chamber syringe of claim 21, further comprising one or more protrusions formed on the barrier, wherein the protrusions are configured to promote mixing.

* * * * *